United States Patent [19]
Ellman et al.

[11] Patent Number: 5,505,728
[45] Date of Patent: Apr. 9, 1996

[54] ELECTROSURGICAL STRIPPING ELECTRODE FOR PALATOPHARYNX TISSUE

[76] Inventors: Alan G. Ellman; Jon C. Garito, both of 1135 Railroad Ave., Hewlett, N.Y. 11557

[21] Appl. No.: 370,532

[22] Filed: Jan. 9, 1995

Related U.S. Application Data

[62] Division of Ser. No. 188,795, Jan. 31, 1994.

[51] Int. Cl.$^6$ .................................................. A61B 17/36
[52] U.S. Cl. .............................. 606/39; 606/45; 606/167; 606/170; 606/173
[58] Field of Search ................................ 606/39, 45, 131, 606/132, 167, 168, 169, 170, 171, 172, 173

[56] References Cited

U.S. PATENT DOCUMENTS 4,887,593  12/1989  Wiley et al. .............................. 606/45

*Primary Examiner*—Angela D. Sykes
*Assistant Examiner*—Stephen D. Huang

[57] ABSTRACT

An electrode for use in an electrosurgical procedure to improve snoring and OSAS. The procedure is based on the progressive enlargement of the airspace in the oropharynx to eliminate or reduce obstructions that can occur during sleep, by electrosurgical stripping of layers of the vibrating soft palate, the wide posterior tonsil pillars, and redundant posterior pharyngeal mucosa. In a preferred embodiment, the electrode is characterized by a bare active wire portion suspended between wire supports on an electrode shaft. The tissue stripping is effected with the bare wire, and the adjacent portions of the wire supports and electrode shaft are made insulating to prevent accidental burns to the patient and to allow the physician to use these insulated parts to help position and guide the active wire portion during the surgical procedure.

5 Claims, 2 Drawing Sheets

ELECTROSURGICAL STRIPPING ELECTRODE FOR PALATOPHARYNX TISSUE

This application is a division of application Ser. No. 08/188,795, filed Jan. 31, 1994, now pending.

This invention relates to an electrosurgical electrode for stripping palatopharynx tissue.

BACKGROUND OF THE INVENTION

Snoring is an annoying noise but considered by doctors to be an ailment that can be treated. Obstructive sleep apnea syndrome (OSAS) involves breathing interference while a patient sleeps, and is also an ailment that can be treated. The known treatments for these disorders are:

1. Postural treatment, which requires that a patient inflicted with one of these disorders must sleep on their stomach;
2. Nasal continuous positive airway pressure, in which the patient is fitted with a nose mask supplied with positive pressure and that must be worn for long periods;
3. Palatopharyngoplasty (PPP), which is a major surgical procedure usually done in a hospital under general anesthesia and requires total removal of the uvula, a conical appendix hanging from the free edge of the soft palate. This has not been entirely satisfactory because it is disfiguring, traumatic, causes violent pain with fatigue and hemorrhagic risks, and possible nasal regurgitation.

SUMMARY OF THE INVENTION

An object of the invention is a surgical procedure capable of improving snoring or OSAS but without the undesired results of PPP.

We have invented a novel electrode for use in an electrosurgical procedure to improve snoring and OSAS. This electrosurgical procedure using our novel electrode enables physicians to offer to patients afflicted with snoring or OSAS a treatment that is safe, effective, and ambulant (meaning with local anesthesia).

The procedure using our novel electrode is based on the progressive enlargement of the airspace in the oropharynx to eliminate or reduce obstructions that can occur during sleep, by electrosurgical stripping of layers of the vibrating soft palate, the wide posterior tonsil pillars, and redundant posterior pharyngeal mucosa.

In a preferred embodiment, our novel electrode is characterized by a bare active wire portion suspended between wire supports on an electrode shaft. The tissue stripping is effected with the bare wire, and the adjacent portions of the wire supports and electrode shaft are made insulating to prevent accidental burns to the patient and to allow the physician to use these insulated parts to help position and guide the active wire portion during the surgical procedure. This enables the physician to shave off during multiple visits successive thin superficial layers of the obstructing tissues avoiding gross resection and its concommitant adverse affects.

DETAILED DESCRIPTION OF THE PREFERRED EMBODIMENTS

Figure 1:
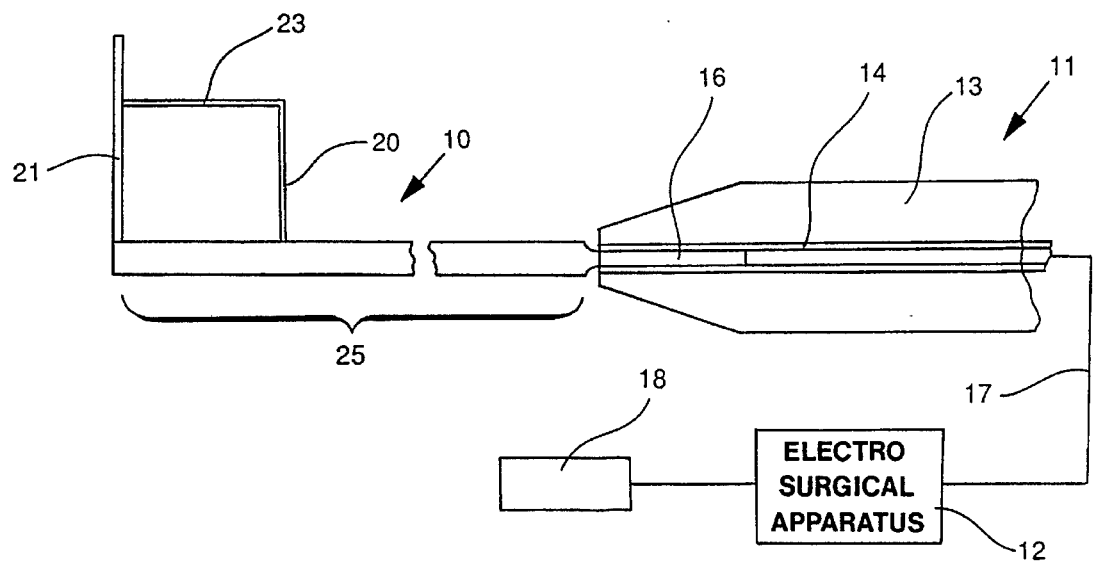
FIG. 1 is a schematic view of one form of palatopharynx stripping electrode of the invention shown mounted in a handpiece connected to electrosurgical apparatus.

FIG. 1 illustrates a preferred form of the novel electrosurgical electrode 10 of the invention mounted in a standard handpiece 11 (only the front end of which is shown) which is connected in the conventional manner to conventional electrosurgical apparatus 12. As an example only, and not meant to be limiting, the handpiece can be a model H6 Surgitron handpiece available from Ellman International, Inc. of Hewlett, N.Y., and the electrosurgical apparatus can be model AAOP Surgitron FFPF available from the same supplier. The Ellman equipment is preferred due to its high operating frequency, typically exceeding 1.5 MHz. Such handpieces 11 conventionally comprise an electrically insulating pen-like member 13 having an electrically conductive tube 14 running lengthwise through it and configured to receive the bare metal shaft 16 of the electrosurgical electrode 10. Not shown are the conventional collet type fittings at the handpiece front to hold the metal shaft in position and to establish the desired electrical connection thereto. The opposite end of the electrically conductive tube 14 is connected by way of a cable 17 to the electrosurgical apparatus 12. Also connected to the latter is the usual indifferent plate 18 which during use is in contact with the patient's body. When the electrosurgical apparatus is energized, high frequency electrosurgical currents are generated which are coupled by way of the electrically conductive tube 14 of the handpiece to the electrode 10. The physician, in the usual way, holds the handpiece while applying the working end of the electrode to the desired area of the patient to be treated.

In accordance with the present invention, the electrosurgical electrode comprises the straight shaft 16 having at one end, the right end, the bare portion to provide good electrical connection to the handpiece, and at the opposite or working end two transversely extending, parallel, wire support members 20, 21. the member 20, which is nearer to the handpiece 11, is shorter than the member 21 which is at the end of the shaft 16. An active electrode metal wire 23, which is bare, is mounted between the end of the shorter member 20 and the other wire support member 21 and parallel to the shaft 16. Each of the wire support members 20, 21 are constituted preferably of thin metal tubes welded or brazed to the metal shaft 16, and the active wire 23 is also brazed or welded to the metal wire support members so that the wire 23 becomes electrically connected to the shaft 16 and any electrosurgical currents conveyed to the shaft are in turn available at the active wire 23. While it is convenient that both members 20, 21 are of metal, this is not essential since only one need be electrically conductive to make the wire 23 active.

In accordance with a feature of the invention, the shaft portion 25 extending from its free end to the handpiece 11 is covered with a coating 26 of an electrically insulating material, which may be one of many suitable electrically insulating plastics, Teflon being one example. Similarly, the full length of the wire support members 20, 21 are also coated 27 with an electrically insulating material.

Figure 2:
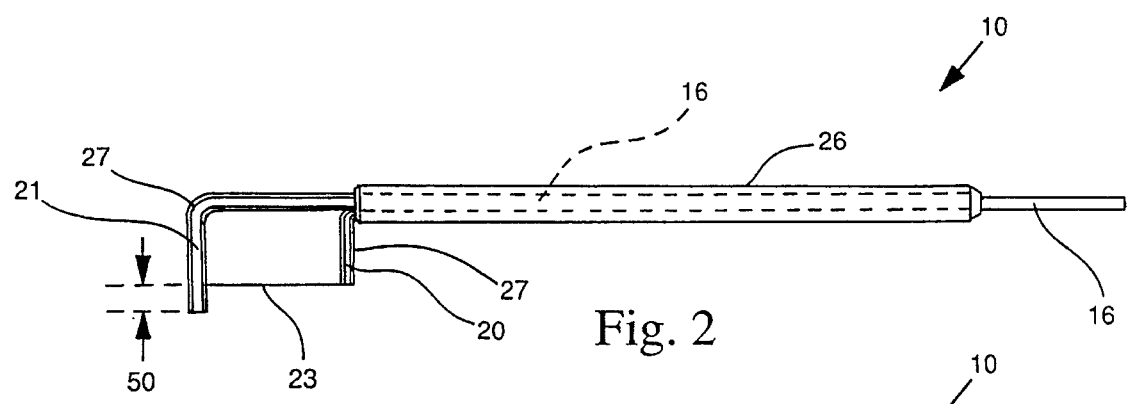
FIGS. 2 and 3 are side and top views, respectively, of the electrode of FIG. 1.
Figure 3:
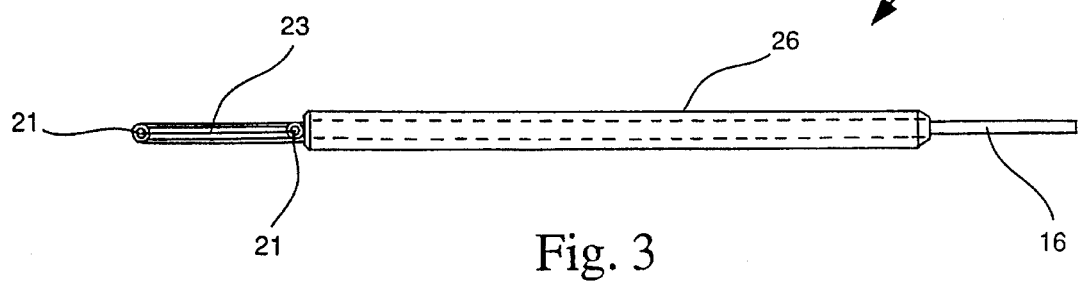
Figure 5:
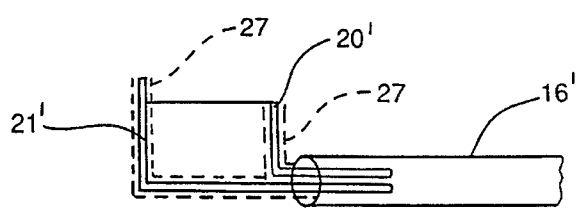
FIG. 5 is a view illustrating one way of fabricating the electrode of FIG. 1.

FIGS. 2 and 3 show this more clearly. In this embodiment, a metal tube constituting the shaft 16 extends lengthwise through the electrode and is bent down (in FIG. 2) to form the wire support member 21, and the other wire support member 20 is connected to the wire support member 21, as by brazing, welding or crimping. In the modification illustrated in FIG. 5, a metal tube 16' has inserted into its free end two generally L-shaped tubes 20', 21' to form the wire support members, and are fixed in the tube 16' in an electrically conductive manner. The electrically insulating coatings are shown here, for clarity, in dashed form.

Figure 4:
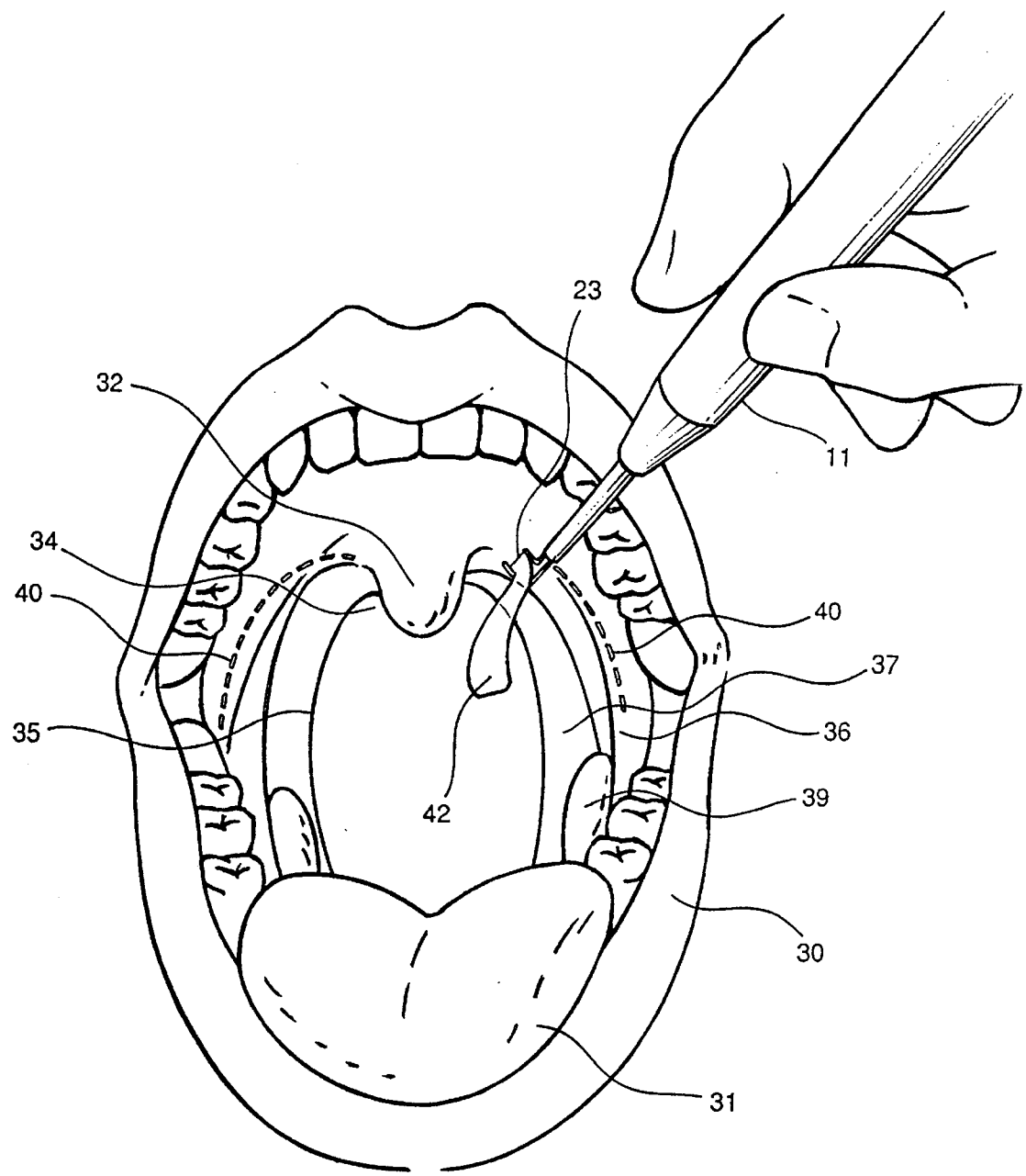
FIG. 4 is a perspective view showing how the electrode of FIG. 1 is used in a surgical procedure.

The reasons for the electrode shape will be clearer from a description of one form of the surgical procedure with reference to FIG. 4, which shows the open mouth of a patient 30 with projecting tongue 31 and hanging uvula 32. Other structural features are the oral pharynx 34, the palatopharyngeal arch 35, the palatoglossal arch 36, the supratonsillar fossa 37, and the pallatine tonsil 39.

After the patient has been pre-medicated with an appropriate oral analgesia and placed in a seating position with mouth open and under local anesthesia, the surgeon turns on the electrosurgical apparatus 12 and by applying the instrument as shown realizes with the active wire 23 a gradual electrosurgical stripping with carbonization for the full length of the superficial layer of the wide lateral pharyngeal walls and low arched soft palate on both sides of the uvula, sparing the uvula. The area to be shaved is marked by the line of rectangles 40. FIG. 4 shows a shaved section 42 which had been stripped off. The procedure is repeated over a number of sessions, each time removing only a thin superficial layer, and allowing the tissue to heal before repeating the procedure. The procedure produces vertical "trenches" laterally at the root of the uvula, creating a new uvula that is smaller and higher, with progressive retraction, after each session. The procedure does not actually realize a resection of the soft tissue, but only a carbonization of the superficial layer progressive and successive at each session, analogous to the peeling of an onion. The electrosurgical application can be extended to the palatine tonsils, if by their large volume they are contributing to snoring by obstructing the oropharynx, and to the posterolateral pharyngeal walls, toward the hypopharynx, if it is an area of collapse of the pharynx. With the Ellman equipment, the fully rectified or cut/coag current is used at a power setting of about 3–4. With the wire electrode 23, a true "onion-slice cut" of the palatopharyngeal arch can be made, with gradual widening of the velopharyngeal isthmus. Usually 5–7 sessions of 5–7 minutes each are needed, spaced 2–3 weeks part. There is very little trauma and the "sore throat" felt by the patient is easily handled by analgesia and anti-inflammatory drugs.

From FIG. 4 it will be clear that the electrically insulating coatings on the shaft 16 and wire support members 20,21 function to prevent undesired contact and possible burns by those members to adjoining and surrounding tissue. The free end 50 of the longer wire support member 21 acts as a backstop and prevents the soft, flexible uvula from being touched with high frequency electrosurgical currents.

The procedure is effective to reduce snoring, which is often due to a rapidly moving stream of air causing vibrations of the soft palate and posterior tonsil pilars. There may also be a pharyngeal narrowing or collapse due to the airway obstruction by a decrease in muscle tone of the pharynx, palate and tongue. The procedure described can be effective in reducing the effects of these disorders, and offers the advantages of avoiding the use of expensive lasers, hospitalization, and much patient trauma, pre-surgery and post-surgery.

As one example of a suitable electrode, which is not meant to be limiting, the length of the shaft 16 was about 4 inches, the active wire 23 was spaced 1 cm from the shaft and was 1½ cm long, and the longer wire support 21 was 1.25 cm long. It will be understood that the electrode of the invention is not limited to its use for stripping palatopharynx tissue. To those skilled in this art, there will certainly be other uses for this novel electrode that provides an active wire arranged parallel to and spaced from the shaft, suspended from two insulated posts for accurately guiding and controlling the position of the active wire during a tissue shaving electrosurgical procedure.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A surgical procedure for treating a human patient having an oral cavity leading to an airspace in an oral pharynx and bounding the airspace wide lateral pharyngeal walls of tissue and low arched soft palate tissue on both sides of an uvula, said patient suffering from snoring or obstructive sleep apnea syndrome as a result of obstructions of the airspace in its oral pharynx, comprising the step of:

(a) reducing snoring or sleep apneas by electrosurgically stripping layers of tissue of the wide lateral pharyngeal walls and low arched soft palate on both sides of the uvula, step (a) being carried out via the oral cavity of the patient while sparing the uvula.

2. The procedure of claim 1, wherein step (a) is carried out by repeating electrosurgically stripping layers of tissue over a number of sessions removing only a thin superficial layer of tissue of the wide lateral pharyngeal walls and low arched soft palate on both sides of the uvula and allowing the tissue to heal before repeating electrosurgically stripping layers of tissue.

3. The procedure of claim 2, wherein the patient has palatine tonsil tissue, and further comprising the step of extending electrosurgical stripping layers of tissue to the tissue of the palatine tonsils.

4. The procedure of claim 2, wherein the patient has posterolateral pharyngeal walls of tissue, and further comprising the step of extending electrosurgically stripping of layers of tissue to tissue of the posterolateral pharyngeal walls.

5. The procedure of claim 1, wherein the electrosurgically stripping is carried out using an exposed cutting wire.

\* \* \* \* \*